(12) United States Patent
Nakamura et al.

(10) Patent No.: US 7,507,038 B2
(45) Date of Patent: Mar. 24, 2009

(54) OPTICAL FIBER/GLASS TUBE FUSION-SPLICED STRUCTURE, OPTICAL FIBER ASSEMBLY INCLUDING THE STRUCTURE, AND GLASS TUBE USED IN THE STRUCTURE

(75) Inventors: Mamoru Nakamura, Hyogo (JP); Takeshi Satake, Hyogo (JP); Motohiko Yamasaki, Hyogo (JP); Moriyuki Fujita, Tokyo (JP); Kenji Sato, Tokyo (JP); Yoshiki Yamakawa, Tokyo (JP)

(73) Assignee: Mitsubishi Cable Industries, Ltd. (JP)

( * ) Notice: Subject to any disclaimer, the term of this patent is extended or adjusted under 35 U.S.C. 154(b) by 0 days.

(21) Appl. No.: 11/730,743

(22) Filed: Apr. 3, 2007

(65) Prior Publication Data

US 2008/0247714 A1 Oct. 9, 2008

(51) Int. Cl.
*G02B 6/255* (2006.01)

(52) U.S. Cl. .............................. 385/96; 385/31; 606/15

(58) Field of Classification Search .................. 385/96, 385/31, 901, 47, 39; 606/15, 16
See application file for complete search history.

(56) References Cited

U.S. PATENT DOCUMENTS

| | | | | |
|---|---|---|---|---|
| 5,292,320 A | * | 3/1994 | Brown et al. | 606/15 |
| 5,343,543 A | * | 8/1994 | Novak et al. | 385/31 |
| 5,428,699 A | | 6/1995 | Pon | |
| 5,509,917 A | * | 4/1996 | Cecchetti et al. | 606/15 |
| 5,537,499 A | * | 7/1996 | Brekke | 385/31 |
| 5,772,657 A | * | 6/1998 | Hmelar et al. | 606/15 |
| 6,564,087 B1 | * | 5/2003 | Pitris et al. | 600/478 |
| 2007/0106286 A1 | * | 5/2007 | Harschack et al. | 606/17 |

FOREIGN PATENT DOCUMENTS

| | | |
|---|---|---|
| JP | 60-108804 | 6/1985 |
| JP | 10-155806 | 6/1998 |

* cited by examiner

*Primary Examiner*—Hemang Sanghavi
(74) *Attorney, Agent, or Firm*—Studebaker & Brackett PC; Donald R. Studebaker (57) ABSTRACT

An optical fiber/glass tube fusion spliced structure includes an optical fiber made of glass and a glass tube through which the optical fiber is inserted and at least in part of the optical fiber/glass tube fusion spliced structure, an outer circumference portion of the optical fiber and an inner circumference portion of the glass tube are fusion spliced. Part of the fusion spliced portion located in one of the optical fiber and the glass tube is formed of a material having a lower fusion point than a fusion point of part of the fusion spliced portion located in the other.

18 Claims, 10 Drawing Sheets

OPTICAL FIBER/GLASS TUBE FUSION-SPLICED STRUCTURE, OPTICAL FIBER ASSEMBLY INCLUDING THE STRUCTURE, AND GLASS TUBE USED IN THE STRUCTURE

BACKGROUND OF THE INVENTION

1. Field of the Invention

The present invention relates to an optical fiber/glass tube fusion-spliced structure and an optical fiber assembly including the structure and a glass tube used in the structure.

2. Description of the Prior Art

In the fields of medicine and machining, optical fibers for transmission of light such as laser beam are widely used in medical surgeries and machining process. In some cases, optical fibers including a light output end is covered with a glass tube whose one end is sealed are used (see, for example, U.S. Pat. No. 5,428,699, Japanese Laid-Open Publication No. 60-108804 and Japanese Laid Open Publication No. 10-155806).

However, when an optical fiber is fusion-spliced with a glass tube to form a united body, the optical fiber is structurally changed a lot and, as a result of such a major structural change, incident characteristics of the optical fiber are influenced.

SUMMARY OF THE INVENTION

An optical fiber/glass tube fusion spliced structure according to the present invention includes an optical fiber made of glass, a glass tube through which the optical fiber is inserted. In the structure, at least in part of the optical fiber/glass tube fusion spliced structure, an outer circumference portion of the optical fiber and an inner circumference portion of the glass tube are fusion spliced. Part of the fusion spliced portion located in one of the optical fiber and the glass tube is formed of a material having a lower fusion point than a fusion point of part of the fusion spliced portion located in the other.

According to the present invention, the part of the fusion spliced portion located in one of the optical fiber and the glass tube is formed of a material having a lower fusion point than the fusion point of part of the fusion spliced portion located in the other or a material having a higher light absorption performance for laser beam having a predetermined wavelength than a light absorption performance of the part of the fusion spliced portion of the other. Thus, if only the fusion spliced portion made of the material having a lower fusion point or the material having a higher light absorption performance for laser beam having a predetermined wavelength is fusion spliced, a major structural change due to fusion of both of the optical fiber and the glass tube can be avoided and light output characteristics of the optical fiber are not influenced by such a structural change.

Other features and advantages of the present invention will be apparent upon reading of the following description with the accompanied drawings.

DETAILED DESCRIPTION OF THE PREFERRED EMBODIMENTS

Hereafter, embodiments will be described in detail with reference to the accompanying drawings.

Embodiment 1

Figure 1:
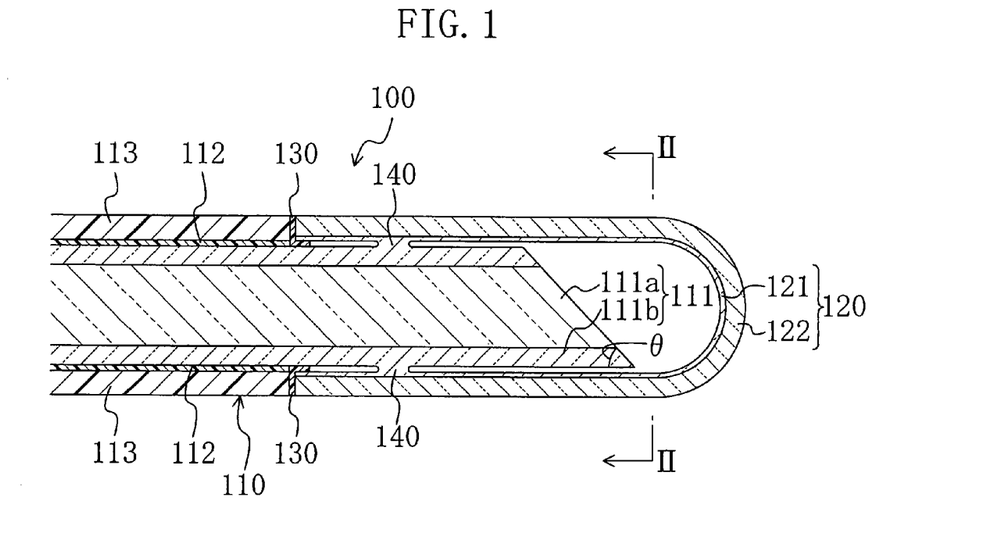
FIG. 1 is a longitudinal-sectional view of an optical fiber/glass tube fusion spliced structure according to Embodiment 1.
Figure 2:
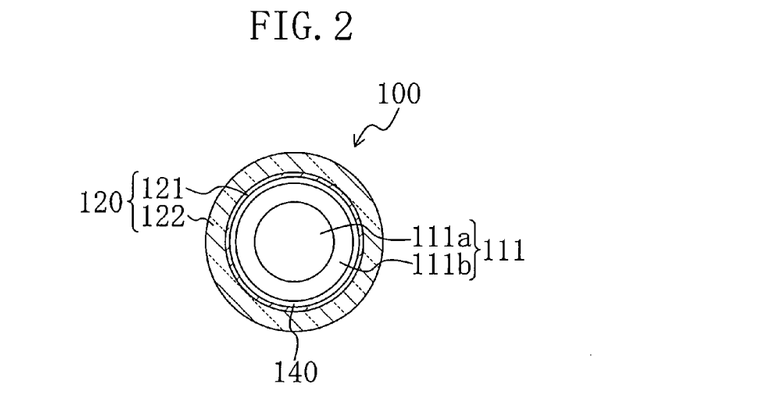
FIG. 2 is a cross-section taken along the line II-II of FIG. 1.

FIGS. 1 and 2 illustrate an optical fiber/glass tube fusion spliced structure 100 according to Embodiment 1. The optical fiber/glass tube fusion spliced structure 100 is a light output end side structure of an optical fiber assembly used for transmission of light such as laser beam.

The optical fiber/glass tube fusion spliced structure 100 includes a covered fiber 110 and a glass tube 120 provided at an end of the covered fiber 110.

The covered fiber 110 includes an optical fiber 111, a buffer layer 112 provided so as to cover an outer circumference surface of the optical fiber 111 and a cover layer 113 of nylon resin or the like for further covering the buffer layer 112. The covered fiber 110 is formed, for example, so that a covered fiber diameter which is an outer diameter of the cover layer 113 is 250-3000 µm.

The optical fiber 111 is made of glass and includes a core 111a which is a fiber core and a clad 111b for covering the core 111a. The optical fiber 111 is formed, for example, so as to have a core diameter of 10-2400 µm and a clad diameter of 25-2500 µm.

The buffer layer 112 is formed, for example, of an ultra-violet cure resin or the like so as to have an outer diameter of 200-2700 µm.

The covered fiber 110 has a configuration in which the buffer layer 112 and the cover layer 113 are sealed from the light output end of the covered fiber 110 and an end portion of the optical fiber 111 protrudes. For example, the protruding end portion of the optical fiber 111 has a length of 100 mm or less. Moreover, an end face of the protruding end portion of the optical fiber 111 is formed to be a flat surface tilted from a fiber axis. An inclination angle θ is, for example, 0-45 degrees. Specifically, it is preferably 38±1 degrees.

The glass tube 120 is made of glass so as to have a cap shape having one end with an opening and the other end sealed. For example, the glass tube 120 is formed so as to have a length of 5-100 mm, an outer diameter of 30-5000 μm and an inner diameter of 25-2500 μm. The glass tube 120 is provided so that the protruding end portion of the optical fiber 111 is inserted from the opening at one end of the glass tube 120 and the glass tube 120 covers the end portion of the optical fiber 111. One end of the glass tube 120 is adhered to respective ends of the buffer layer 112 and the cover layer 113 with an adhesive 130 therebetween and an opening portion is adhered to a base of the end portion of the optical fiber 111 with the adhesive 130 therebetween. As the adhesive 130, for example, epoxy resin, silicon resin, acrylic resin or the like can be used.

In parts of the optical fiber 111 and the glass tube 120 located closer to the sealed end of the glass tube 120 than the above-described adhered part, an outer circumference portion of the optical fiber 111 and an inner circumference portion of the glass tube 120 each extending along an entire circumference are fusion spliced to form a fusion spliced portion 140.

Each of the optical fiber 111 and the glass tube 120 is made of glass. As for the optical fiber 111, the core 111a is formed of a material having a larger refractive index than a refractive index of the clad 111b. The glass tube 120 is formed so as to have a two-layer structure including an inner layer 121 and an outer layer 122. The inner layer 121 is formed of a material having a lower fusing point than respective fusing points of the outer layer 122 and the clad 111b of the optical fiber 111. As such a structure, for example, used is a structure in which the optical fiber 111 includes the core 111a formed of quartz doped with Ge or the like at 20 mol % or less to obtain a high refractive index and the clad 111b formed of pure quartz and the glass tube 120 includes the inner layer 121 formed of quartz doped with fluorine, $BF_3$ or the like at 20 mol % to obtain a low fusing point and the outer layer 122 formed of pure quartz. In this case, in the optical fiber 111, a refractive index of the core 111a is 1.45-1.46, a refractive index of the clad 111b is 1.44-1.47 and a fusing point of the clad 111b is 1400° C. or more. In the glass tube 120, a fusing point of the inner layer 121 is 900° C. or more and a fusing point of the outer layer 122 is 1400° C. or more.

In the optical fiber/glass tube fusion spliced structure 100 having the above-described structure, light from a light source such as a laser is confined in the core 111a of the optical fiber 111, transmitted, reflected at the tilted end face of the optical fiber 111 in the light output end, and output from a side surface of the glass tube 120 through the clad 111b and the glass tube 120 functioning as a collective lens. At this time, even if laser beam is reflected diffusely and the like and a substance is liberated from the adhesive 130 between the covered fiber 110 and the glass tube 120 due to the diffuse reflection, the parts of the optical fiber 111 and the glass tube 120 located closer to the sealed end than the adhered part and extending along an entire circumference are fusion spliced and thus the substance does not enter in a region between the end portion of the optical fiber 111 and the glass tube 120. Therefore, light transmission is not influenced.

Next, a method for forming the light output end side structure of the optical fiber/glass tube fusion spliced structure 100 will be described with reference to FIGS. 3A through 3E.

Figure 3A:
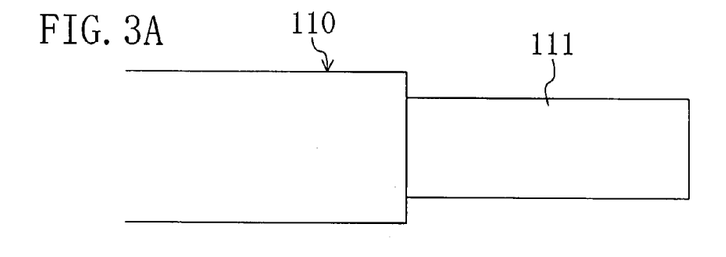
FIGS. 3A through 3E are cross-sectional views illustrating respective steps for forming the optical fiber/glass tube fusion spliced structure of Embodiment 1.

First, as shown in FIG. 3A, at a light output end side of the covered fiber 110, parts of the buffer layer 112 and the cover layer 113 having a predetermined length are scaled so that an end portion of the optical fiber 111 protrudes and is exposed.

Figure 3B:
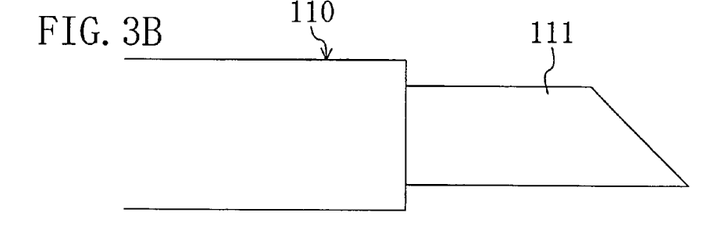

Next, as shown in FIG. 3B, an end face of the optical fiber 111 is made into a flat surface tilted from a fiber axis.

Figure 3C:
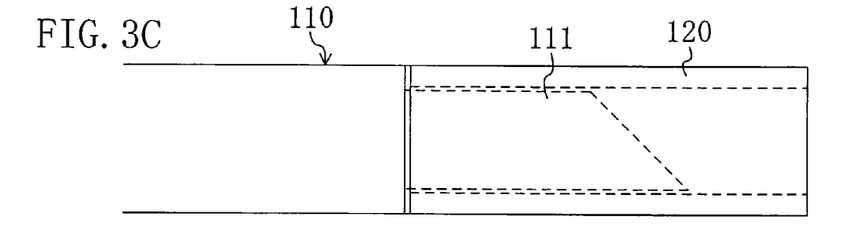

Next, as shown in FIG. 3C, the end portion of the optical fiber 111 is inserted into the glass tube 120 from one end thereof and an end face of the glass tube 120 is adhered to respective end faces of the buffer layer 112 and the cover layer 113 with the adhesive 130 and the opening portion of the glass tube 120 and the base of the end portion of the optical fiber 111 are adhered with the adhesive 130.

Figure 3D:
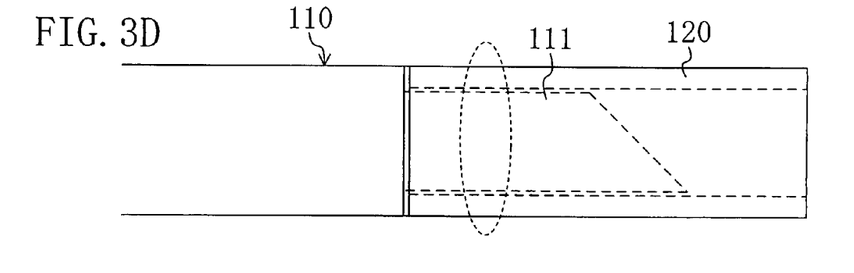

Next, as shown in FIG. 3D, in part of the optical fiber/glass tube fusion spliced structure 100 located closer to an end thereof than the above-described adhered part, by applying heat using laser ($CO_2$ laser or the like), a gas torch, discharge, an electrothermal heater or the like from the outside to an entire circumference of the covered fiber 110, the optical fiber 111 and the glass tube 120 each extending along an entire circumference are fusion spliced to form a fusion spliced portion 140. At this time, a heating temperature is set to be a temperature equal to or higher than a fusion point of the inner layer 121 of the glass tube 120 and lower than respective fusion points of the outer layer 122 and the clad 111b of the optical fiber 111. Thus, only the inner layer 121 of the glass tube 120 is fused with the optical fiber 111 which has not been fusion spliced. Therefore, a major structural change due to fusion of both of the optical fiber 111 and the glass tube 120 can be avoided and light output characteristics of laser beam are not influenced by such a structural change.

Figure 3E:
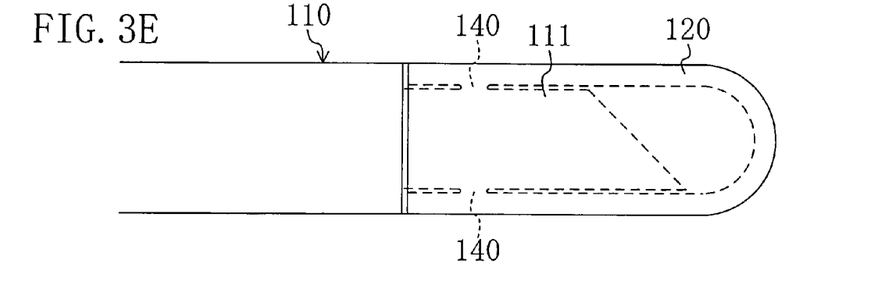

Then, as shown in FIG. 3E, an opening at the other end of the glass tube 120 is heated and sealed using laser (specifically, $CO_2$ laser), a gas torch, discharge, an electrothermal heater or the like so that the other end of the glass tube 120 has a cap shape.

Figure 4:
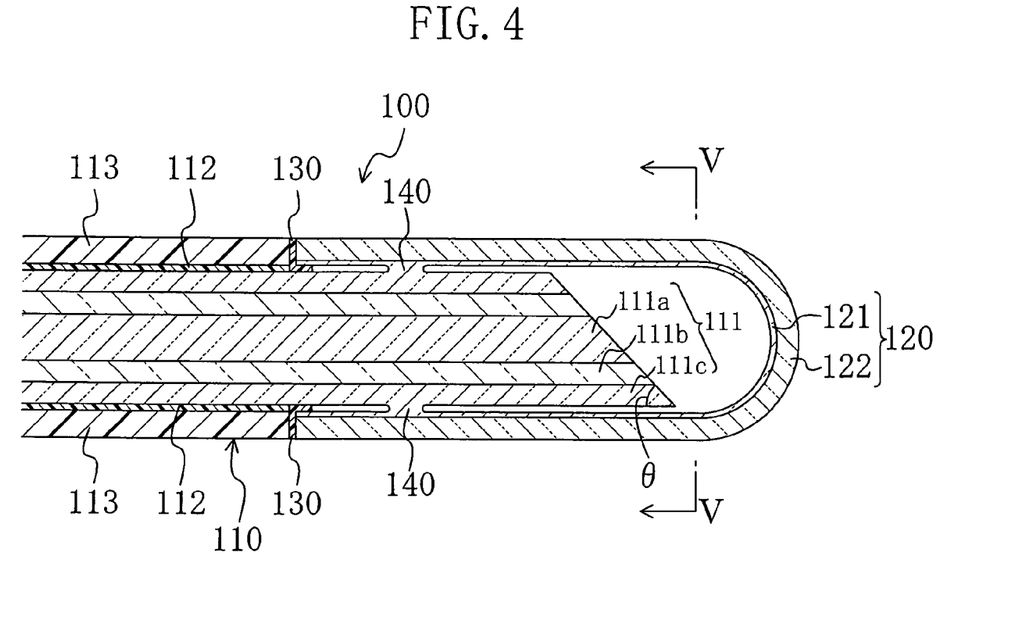
FIG. 4 is a longitudinal-sectional view of an optical fiber/glass tube fusion spliced structure according to a modified example of Embodiment 1 and Embodiment 2.
Figure 5:
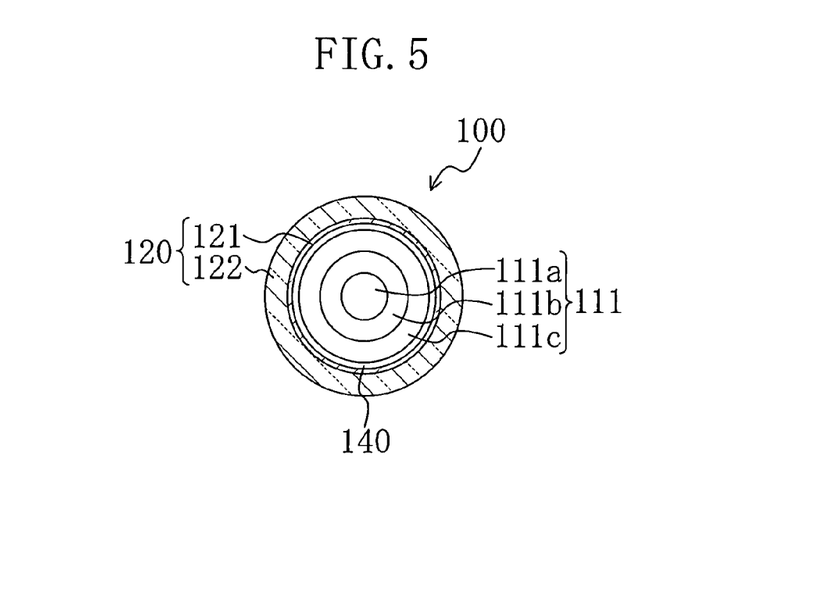
FIG. 5 is a cross-section taken along the line V-V of FIG. 4.

In Embodiment 1, the optical fiber 111 includes the core 111a and the clad 111b and the inner layer 121 of the glass tube 120 is formed of a material having a lower fusion point than respective fusion points of the outer layer 122 and the clad 111b of the optical fiber 111. As a modified example of Embodiment 1, as shown in FIG. 4 and FIG. 5, the optical fiber 111 may further include a supporting layer 111c for covering the clad 111b and the inner layer 121 of the glass tube 120 may be formed of a material having a lower fusion point than respective fusion points of the outer layer 122 and the supporting layer 111c of the optical fiber 111. As such a structure, for example, the optical fiber 111 includes the core 111a formed of pure quartz, the clad 111b formed of quartz doped with fluorine, $BF_3$ or the like at 20 mol % or less to obtain a low refractive index and the supporting layer 111c formed of pure quartz, and the glass tube 120 includes the inner layer 121 formed of quartz doped with fluorine, $BF_3$ or the like at 20 mol % or less to obtain a low refractive index and the outer layer 122 formed of pure quartz. In this case, in the optical fiber 111, the refractive index of the core 111a is 1.45-1.46, the refractive index of the clad 111b is 1.44-1.47, the refractive index of the supporting layer 111c is 1.45-1.46, and a fusion point of the supporting layer 111c is 1400° C. or more. In the optical fiber 111, for example, the core layer has a diameter of 10-2400 μm, the clad layer has a diameter of 25-2500 μm and the supporting layer has a diameter of 30-2600 μm.

As has been described, the optical fiber 111 includes the supporting layer 111c located at an outer side of the clad 111b. Thus, breaks in the structure of the optical fiber 111 can be suppressed.

Embodiment 2

An optical fiber/glass tube fusion spliced structure 100 according to Embodiment 2 has the same outer appearance as that in Embodiment 1 and therefore will be described with reference to FIG. 1 and FIG. 2.

In this optical fiber/glass tube fusion spliced structure 100, an optical fiber 111 includes a core 111a formed of a material having a higher refractive index than a refractive index of a clad 111b. Moreover, a glass tube 120 is formed so as to have a two-layer structure including an inner layer 121 and an outer layer 122 and the inner layer 121 is formed of a material having a higher light absorption performance for laser beam having a predetermined wavelength than respective light absorption performances of the outer layer 122 and the clad 111b of the optical fiber 111. As such a structure, for example, the optical fiber 111 includes a core 111a formed of quartz doped with Ge or the like at 20 mol % or less to obtain a high refractive index and the clad 111b formed of pure quartz, and the glass tube 120 includes the inner layer 121 formed of lead glass or quartz having an OH value of 700 ppm or more and a high laser beam absorption performance and the outer layer 122 formed of pure quartz. In this case, the inner layer 121 of the glass tube 120 has a high light absorption performance for laser beam having a wavelength of 9.2-10.8 μm and, on the other hand, the outer layer 122 and the clad 111b of the optical fiber 111 has a very low light absorption performance for laser beam having a wavelength of 9.2-10.8 μm.

In forming the optical fiber/glass tube fusion spliced structure 100, in part of the covered fiber 110 located closer to an end of thereof than adhered part between the optical fiber 111 and the glass tube 120, by irradiating laser beam having a predetermined wavelength to the part from the outside, parts of the optical fiber 111 and the glass tube 120 each extending along an entire circumference are fusion spliced to form a fusion spliced portion 140. At this time, a wavelength of laser beam is set so that the inner layer 121 exhibits a high light absorption performance for the laser beam and the outer layer 122 and the clad 111b of the optical fiber 111 exhibits a very low light absorption performance for the laser beam. Thus, only the inner layer 121 of the glass tube 120, which is formed of a material having a high laser beam absorption performance, is fusion spliced with the optical fiber 111 which has not been fused. Therefore, a major structural change due to fusion of both of the optical fiber 111 and the glass tube 120 can be avoided and light output characteristics of laser beam are not influenced by such a structural change.

In Embodiment 2, the optical fiber 111 includes the core 111a and the clad 111b and the inner layer 121 of the glass tube 120 is formed of a material having a high light absorption performance for laser beam having a predetermined wavelength than respective light absorption performances of the outer layer 122 and the clad 111b. As a modified example of Embodiment 2, as shown in FIG. 4 and FIG. 5, the optical fiber 111 may further include a supporting layer 111c for covering the clad 111b and the inner layer 121 of the glass tube 120 may be formed of a material having a higher light absorption performance for laser beam having a predetermined wavelength than respective light absorption performances of the outer layer 122 and the supporting layer 111c of the optical fiber 111. As such a structure, for example, the optical fiber 111 includes the core 111a formed of pure quartz, the clad 111b formed of quartz doped with fluorine, $BF_3$ or the like at 20 mol % or less to obtain a low refractive index and furthermore the supporting layer 111c formed of pure quartz, and the glass tube 120 includes the inner layer 121 formed of lead glass or quartz having an OH value of 700 ppm or more and a high laser beam absorption performance and the outer layer 122 formed of pure quartz. In this case, the inner layer 121 of the glass tube 120 has a high light absorption performance for laser beam having a wavelength of 9.2-10.8 μm and, on the other hand, each of the outer layer 122 and the clad 111b of the optical fiber 111 has a very low light absorption performance for laser beam having a wavelength of 9.2-10.8 μm. In the optical fiber 111, for example, the core layer has a diameter of 10-2400 μm, the clad layer has a diameter of 25-2500 μm and the supporting layer has a diameter of 30-2600 μm.

As has been described, the optical fiber 111 includes the supporting layer 111c at an outer side of the clad 111b. Thus, breaks in the structure of the optical fiber 111 can be suppressed.

Other than that, the structure, operation, formation method and effects of the optical fiber/glass tube fusion spliced structure 100 of Embodiment 2 are the same as those of Embodiment 1.

Embodiment 3

Figure 6:
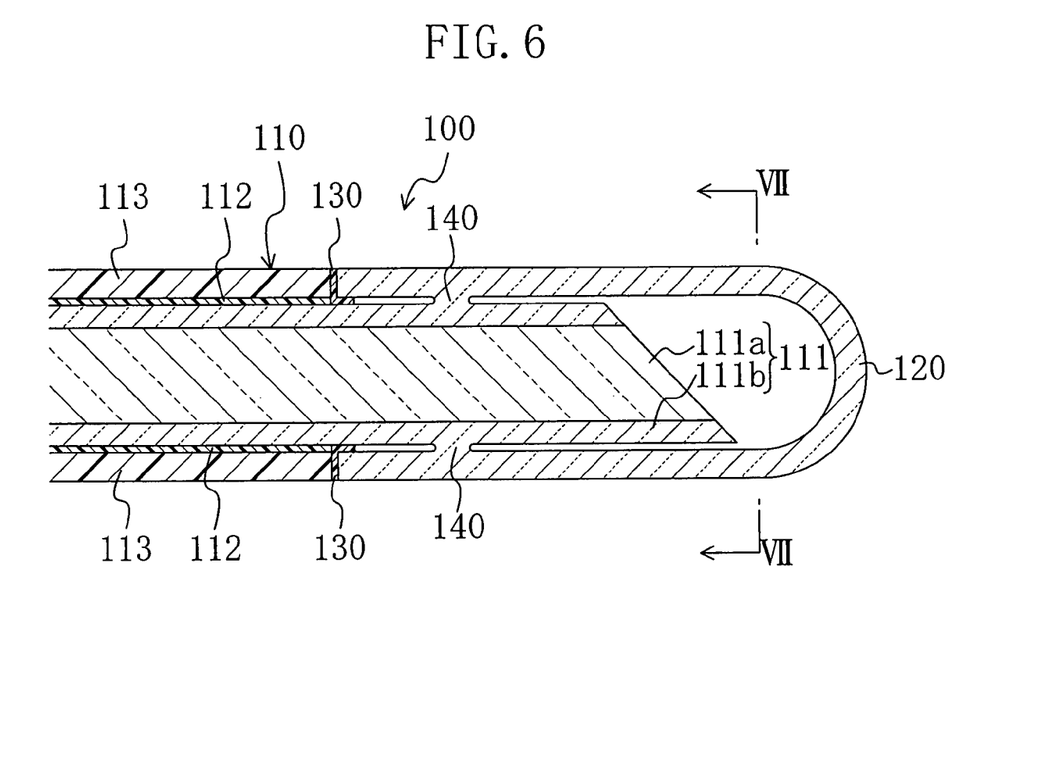
FIG. 6 is a longitudinal-sectional view of an optical fiber/glass tube fusion spliced structure according to Embodiment 3.
Figure 7:
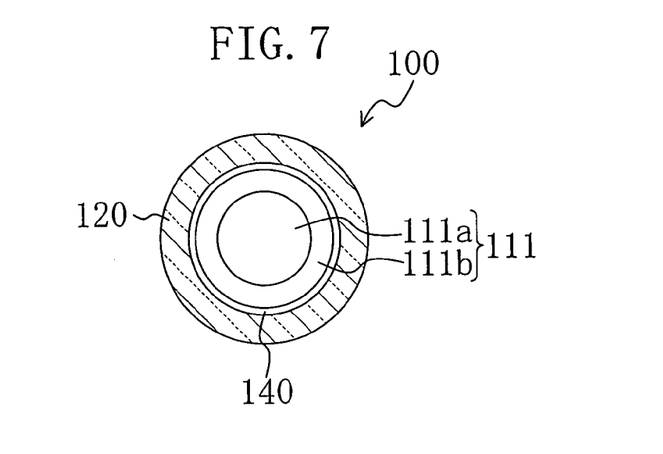
FIG. 7 is a cross-section taken along the line VII-VII of FIG. 6.

FIG. 6 and FIG. 7 illustrate an optical fiber/glass tube fusion spliced structure 100 according to Embodiment 3. Each member also shown in Embodiment 1 is identified by the same reference numeral. Also, the optical fiber/glass tube fusion spliced structure 100 is a light output end side structure of an optical fiber assembly used for transmission of light such as laser beam.

In this optical fiber/glass tube fusion spliced structure 100, an optical fiber 111 includes a core 111a formed of a material having a higher refractive index than a refractive index of a clad 111b. A glass tube 120 is formed of a material having a higher fusion point than a fusion point of the clad 111b of the optical fiber 111 so as to have a single-layer structure. As such a structure, for example, the optical fiber 111 includes the core 111a formed of pure quartz and the clad 111b formed of quartz doped with fluorine, $BF_3$ or the like at 20 mol % or less to obtain a low refractive index and a low fusion point and the glass tube 120 formed of pure quartz. In this case, in the optical fiber 111, a refractive index of the core 111a is 1.45-1.46, a refractive index of the clad 111b is 1.44-1.47 and a fusing point of the clad 111b is 900° C. or more. In the glass tube 120, a fusing point of the outer layer 122 is 1400° C. or more.

In forming the optical fiber/glass tube fusion spliced structure 100, in part of the covered fiber 110 located closer to an end thereof than adhered part between the optical fiber 111 and the glass tube 120, by applying laser ($CO_2$ laser or the like), a gas torch, discharge, an electrothermal heater or the like from the outside to heat an entire circumference of the covered fiber 110, the optical fiber 111 and the glass tube 120 each extending along an entire circumference are fusion spliced to form a fusion spliced portion 140. At this time, a heating temperature is set to be a temperature equal to or higher than a fusion point of the clad 111b of the optical fiber 111 and lower than a fusion point of the glass tube 120. Thus, only the clad 111b of the optical fiber 111 is fused with the glass tube 120 which has not been fusion spliced. Therefore, a major structural change due to fusion of both of the optical fiber 111 and the glass tube 120 can be avoided and light output characteristics of laser beam are not influenced by such a structural change.

Other than that, the structure, operation, formation method and effects of the optical fiber/glass tube fusion spliced structure 100 of Embodiment 3 are the same as those of Embodiment 1.

Embodiment 4

An optical fiber/glass tube fusion spliced structure 100 according to Embodiment 4 has the same outer appearance as that in Embodiment 3 and therefore will be described with reference to FIG. 6 and FIG. 7.

In this optical fiber/glass tube fusion spliced structure 100, an optical fiber 111 includes a core 111a formed of a material having a higher refractive index than a refractive index of a clad 111b. Moreover, a glass tube 120 is formed so as to have a single-layer structure and is formed of a material having a lower light absorption performance for laser beam having a predetermined wavelength than the clad 111b of the optical fiber 111. As such a structure, for example, the optical fiber 111 includes a core 111a formed of pure quartz and the clad 111b formed of lead glass or quartz having an OH value of 700 ppm and a high laser beam absorption performance, and the glass tube 120 formed of pure quartz. In this case, the clad 111b of the optical fiber 111 has a high light absorption performance for laser beam having a wavelength of 9.2-10.8 μm and, on the other hand, the glass tube 120 has a very low light absorption performance for laser beam having a wavelength of 9.2-10.8 μm.

In forming the optical fiber/glass tube fusion spliced structure 100, in part of the covered fiber 110 located closer to an end of thereof than adhered part between the optical fiber 111 and the glass tube 120, by irradiating laser beam having a predetermined wavelength to the part from the outside, parts of the optical fiber 111 and the glass tube 120 each extending along an entire circumference are fusion spliced to form a fusion spliced portion 140. At this time, a wavelength of laser beam is set so that the clad 111b of the optical fiber 111 exhibits a high light absorption performance for the laser beam and the glass tube 120 exhibits a very low light absorption performance for the laser beam. Thus, only the clad 111b of the optical fiber 111, which is formed of a material having a high laser beam absorption performance, is fusion spliced with the glass tube 120 which has not been fused. Therefore, a major structural change due to fusion of both of the optical fiber 111 and the glass tube 120 can be avoided and light output characteristics of laser beam are not influenced by such a structural change.

Other than that, the structure, operation, formation method and effects of the optical fiber/glass tube fusion spliced structure 100 of Embodiment 4 are the same as those of Embodiment 3.

Embodiment 5

Figure 8:
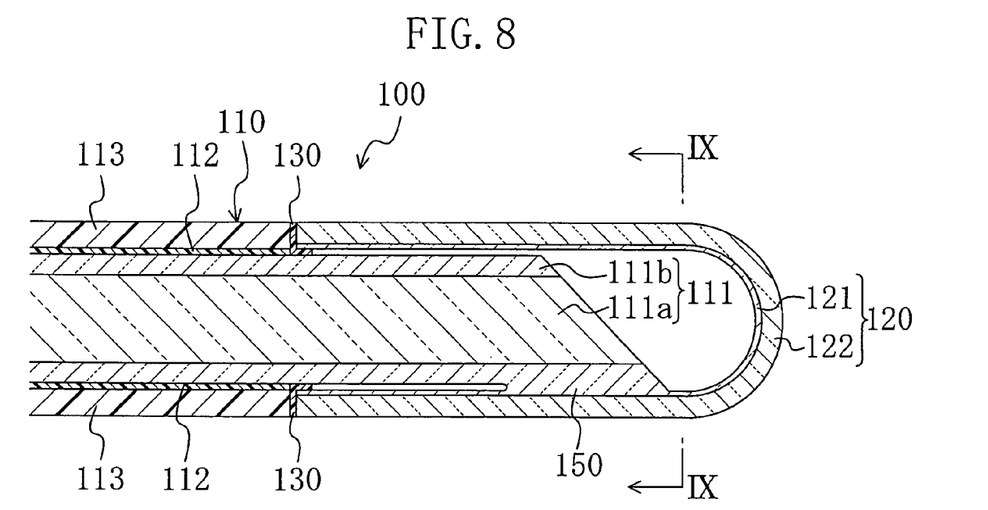
FIG. 8 is a longitudinal-sectional view of an optical fiber/glass tube fusion spliced structure according to Embodiment 5.
Figure 9:
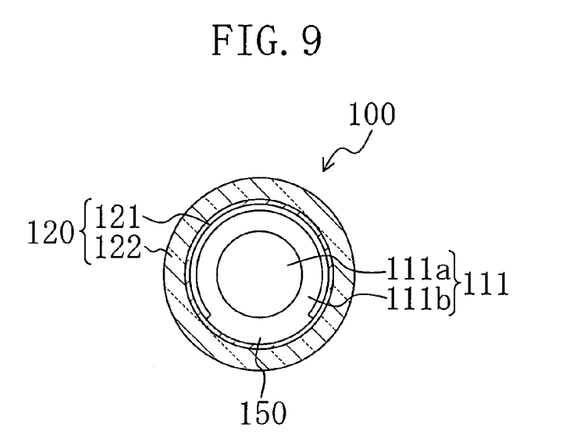
FIG. 9 is a cross-section taken along the line IX-IX of FIG. 8.

FIG. 8 and FIG. 9 illustrate an optical fiber/glass tube fusion spliced structure 100 according to Embodiment 5. Each member also shown in Embodiment 1 is identified by the same reference numeral. The optical fiber/glass tube fusion spliced structure 100 is a light output end side structure of an optical fiber assembly used for transmission of light such as laser beam.

In this optical fiber/glass tube fusion spliced structure 100, the fusion spliced portion 140 extending along an entire circumference of thereof, which has been described in each of Embodiments 1 through 4 is not provided and a fusion spliced portion 150 fusion spliced so as to include light passing through portions in an outer circumference portion of an end portion of an optical fiber 111 and in an inner circumference portion of a glass tube 120.

Each of the optical fiber 111 and the glass tube 120 is made of glass. The optical fiber 111 includes a core 111a formed of a material having a higher refractive index than a refractive index of the clad 111b. Moreover, the glass tube 120 is formed so as to have a two-layer structure including an inner layer 121 and an outer layer 122. The inner layer 121 is formed of a material having a lower fusion point than respective fusion points of the outer layer 122 and the clad 111b of the optical fiber 111. As such a structure, for example, the optical fiber 111 includes the core 111a formed of quartz doped with Ge or the like at 20 mol % or less to obtain a high refraction index and the clad 111b formed of pure quartz, and the glass tube 120 includes the inner layer 121 formed of quartz doped with fluorine, $BF_3$ or the like at 20 mol % or less to obtain a low fusion point and the outer layer 122 formed of pure quartz. In this case, in the optical fiber 111, a refractive index of the core 111a is 1.45-1.46, a refractive index of the clad 111b is 1.44-1.47 and a fusing point of the clad 111b is 1400° C. or more. In the glass tube 120, a fusing point of the inner layer 121 is 900° C. or more and a fusing point of the outer layer 122 is 1400° C. or more.

In the optical fiber/glass tube fusion spliced structure 100 having the above-described structure, the fusion spliced portion 150 is fusion spliced so as to include light passing through portions in the outer circumference portion of the end portion of the optical fiber 111 and in the inner circumference portion of the glass tube 120. Thus, there is no impurity included between them and transmission of light is not influenced by impurities.

Figure 10:
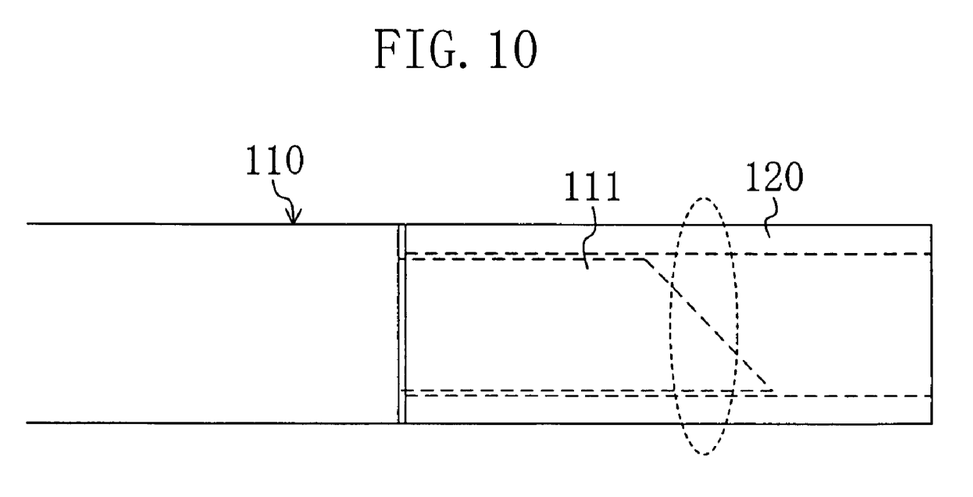
FIG. 10 is a cross-sectional view illustrating respective steps for forming the optical fiber/glass tube fusion spliced structure of Embodiment 5.

In forming the optical fiber/glass tube fusion spliced structure 100, as shown in FIG. 10, in part of the optical fiber/glass tube fusion spliced structure 100 including the light passing through portions in an outer circumference portion of one end of the optical fiber 111 and in an inner circumference portion of the glass tube 120, by applying heat from the outside using laser ($CO_2$ laser or the like), a gas torch, discharge, electro-thermo heater, or the like, the optical fiber 111 and the glass tube 120 are fusion spliced to form the fusion spliced portion 150. At this time, a heating temperature is set to be a temperature equal to or higher than a fusion point of the inner layer 121 of the glass tube 120 and lower than respective fusion points of the outer layer 122 and the clad 111b of the optical fiber 111. Thus, only the inner layer 121 of the glass tube 120 is fusion spliced with the optical fiber 111 which has not been fusion spliced. Therefore, a major structural change due to fusion of both of the optical fiber 111 and the glass tube 120 can be avoided and light output characteristics of laser beam are not influenced by such a structural change.

Figure 11:
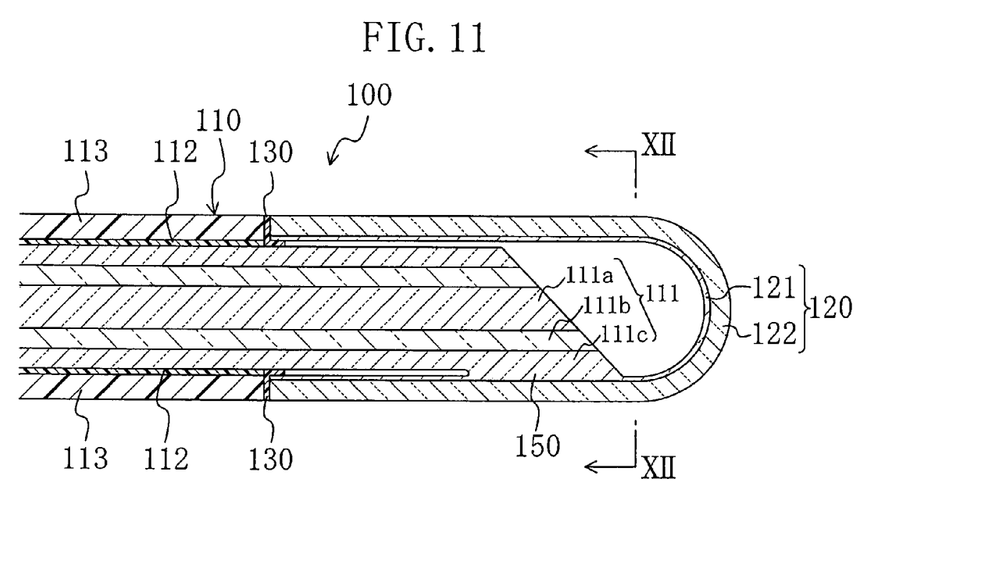
FIG. 11 is a longitudinal-sectional view of an optical fiber/glass tube fusion spliced structure according to a modified example of Embodiment 5 and Embodiment 6.
Figure 12:
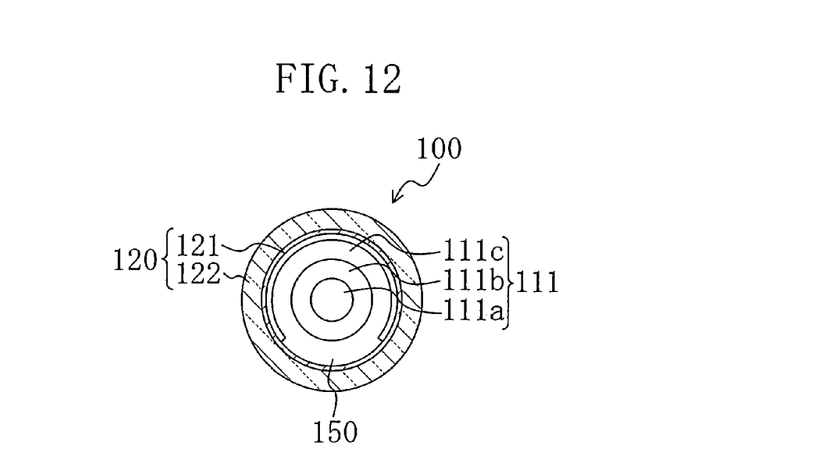
FIG. 12 is a cross-section taken along the line XII-XII of FIG. 11.

In Embodiment 5, the optical fiber 111 includes the core 111a and the clad 111b and the inner layer 121 of the glass tube 120 is formed of a material having a lower fusion point than respective fusion points of the outer layer 122 and the clad 111b of the optical fiber 111. As a modified example of Embodiment 5, as shown in FIG. 11 and FIG. 12, the optical fiber 111 may further include a supporting layer 111c for covering the clad 111b and the inner layer 121 of the glass tube 120 may be formed of a material having a lower fusion point than respective fusion points of the outer layer 122 and the supporting layer 111c of the optical fiber 111. As such a structure, for example, the optical fiber 111 includes the core 111a formed of pure quartz, the clad 111b formed of quartz doped with fluorine, $BF_3$ or the like at 20 mol % or less to obtain a low refractive index and the supporting layer 111c formed of pure quartz, and the glass tube 120 includes the inner layer 121 formed of quartz doped with fluorine, $BF_3$ or the like at 20 mmol % or less to obtain a low fusion point and the outer layer 122 formed of pure quartz. In this case, in the optical fiber 111, a refractive index of the core 111a is 1.45-1.46, a refractive index of the clad 111b is 1.44-1.47, a refractive index of the supporting layer 111c is 1.45-1.46 and a fusing point of the supporting layer 111c is 1400° C. or more. In the glass tube 120, a fusing point of the inner layer 121 is 900° C. or more and a fusing point of the outer layer 122 is 1400° C. or more. In the optical fiber 111, for example, the core layer has a diameter of 10-2400 μm, the clad layer has a diameter of 25-2500 μm and the supporting layer has a diameter of 30-2600 μm.

As has been described, the optical fiber 111 includes the supporting layer 111c located at an outer side of the clad 111b. Thus, breaks in the structure of the optical fiber 111 can be suppressed.

Other than that, the structure, operation, formation method and effects of the optical fiber/glass tube fusion spliced structure 100 of Embodiment 5 are the same as those of Embodiment 1.

Embodiment 6

An optical fiber/glass tube fusion spliced structure 100 according to Embodiment 6 has the same outer appearance as that in Embodiment 1 and therefore will be described with reference to FIG. 8 and FIG. 9.

In this optical fiber/glass tube fusion spliced structure 100, an optical fiber 111 includes a core 111a formed of a material having a higher refractive index than a refractive index of the clad 111b. Moreover, a glass tube 120 is formed so as to have a two-layer structure including an inner layer 121 and an outer layer 122 and the inner layer 121 is formed of a material having a higher light absorption performance for laser beam having a predetermined wavelength than respective light absorption performances of the outer layer 122 and the clad 111b of the optical fiber 111. As such a structure, for example, the optical fiber 111 includes the core 111a formed of quartz doped with Ge or the like at 20 mol % or less and the clad 111b formed of pure quartz, and the glass tube 120 includes the inner layer 121 formed of lead glass or quartz having an OH value of 700 ppm or more and a high light absorption performance and the outer layer 122 formed of pure quartz. In this case, the inner layer 121 of the glass tube 120 has a high light absorption performance for laser beam having a wavelength of 9.2-10.8 μm and, on the other hand, the outer layer 122 and the clad 111b of the optical fiber 111 has a very low light absorption performance for laser beam having a wavelength of 9.2-10.8 μm.

In forming the optical fiber/glass tube fusion spliced structure 100, in part of the optical fiber/glass tube fusion spliced structure 100 including light passing through portions in an outer circumference portion of one end of the optical fiber 111 and in an inner circumference portion of the glass tube 120, by irradiating laser beam having a predetermined wavelength to the part from the outside, the optical fiber 111 and the glass tube 120 are fusion spliced to form a fusion spliced portion 150. At this time, a wavelength of laser beam is set so that the clad 111b of the optical fiber 111 exhibits a high light absorption performance for the laser beam and the glass tube 120 exhibits a very low light absorption performance for the laser beam. Thus, only the inner layer 121 of the glass tube 120, which is formed of a material having a high laser beam absorption performance, is fusion spliced with the optical fiber 111 which has not been fused. Therefore, a major structural change due to fusion of both of the optical fiber 111 and the glass tube 120 can be avoided and light output characteristics of laser beam are not influenced by such a structural change.

In Embodiment 6, the optical fiber 111 includes the core 111a and the clad 111b and the inner layer 121 of the glass tube 120 is formed of a material having a high light absorption performance for laser beam having a predetermined wavelength. As a modified example of Embodiment 6, as shown in FIG. 11 and FIG. 12, the optical fiber 111 may further include a supporting layer 111c for covering the clad 111b and the inner layer 121 of the glass tube 120 may be formed of a material having a higher light absorption performance for laser beam having a predetermined wavelength than respective light absorption performances of the outer layer 122 and the supporting layer 111c of the optical fiber 111. As such a structure, for example, the optical fiber 111 includes the core 111a formed of pure quartz, the clad 111b formed of quartz doped with fluorine, $BF_3$ or the like at 20 mol % or less to obtain a low refractive index and, furthermore, the supporting layer 111c formed of pure quartz, and the glass tube 120 includes the inner layer 121 formed of lead glass or quartz having an OH value of 700 ppm or more and a high laser beam absorption performance and the outer layer 122 formed of pure quartz. In this case, in the glass tube 120, the inner layer 121 has a high light absorption performance for laser beam having a wavelength of 9.2-10.8 μm and, on the other hand, each of the outer layer 122 and the clad 111b of the optical fiber 111 has a very low light absorption performance for laser beam having a wavelength of 9.2-10.8 μm. In the optical fiber 111, for example, the core layer has a diameter of 10-2400 μm, the clad layer has a diameter of 25-2500 μm and the supporting layer has a diameter of 30-2600 μm.

As has been described, the optical fiber 111 includes the supporting layer 111c at an outer side of the clad 111b. Thus, breaks in the structure of the optical fiber 111 can be suppressed.

Other than that, the structure, operation, formation method and effects of the optical fiber/glass tube fusion spliced structure 100 of Embodiment 6 are the same as those of Embodiment 5.

Embodiment 7

Figure 13:
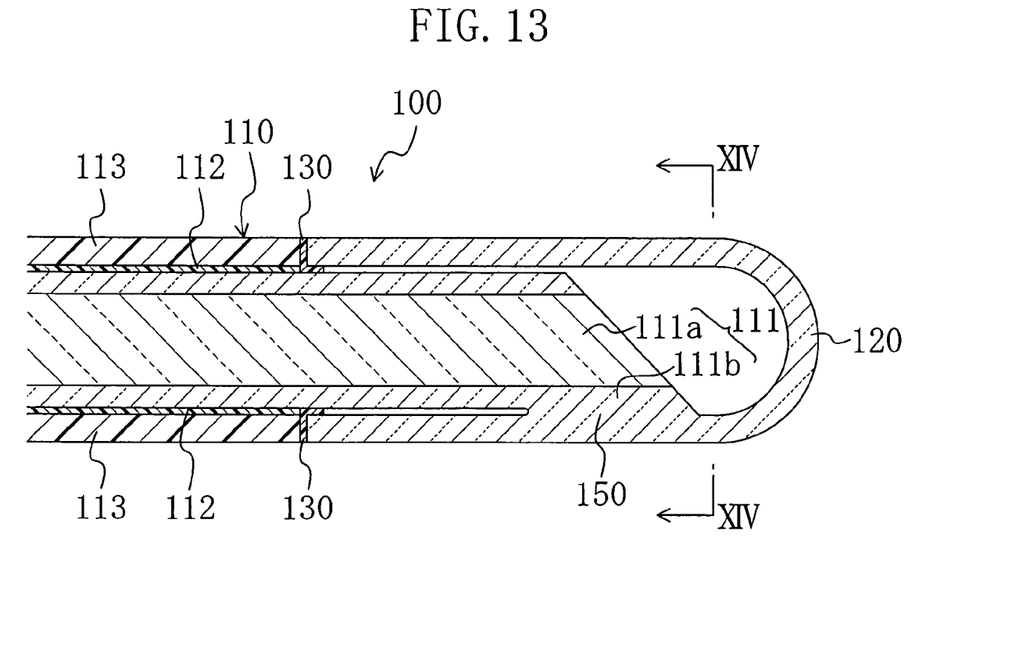
FIG. 13 is a longitudinal-sectional view of an optical fiber/glass tube fusion spliced structure according to Embodiment 7.
Figure 14:
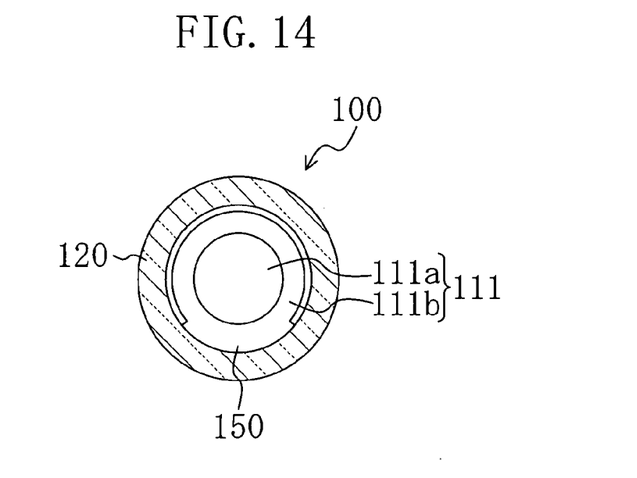
FIG. 14 is a cross-section taken along the line XIV-XIV of FIG. 13.

FIG. 13 and FIG. 14 illustrate an optical fiber/glass tube fusion spliced structure 100 according to Embodiment 7. Each member also shown in Embodiment 1 is identified by the same reference numeral. Also, the optical fiber/glass tube fusion spliced structure 100 is a light output end side structure of an optical fiber assembly used for transmission of light such as laser beam.

In this optical fiber/glass tube fusion spliced structure 100, an optical fiber 111 includes a core 111a formed of a material having a higher refractive index than a refractive index of a clad 111b. A glass tube 120 is formed of a material having a higher fusion point than a fusion point of the clad 111b of the optical fiber 111 so as to have a single-layer structure. As such a structure, for example, the optical fiber 111 includes the core 111a formed of pure quartz and the clad 111b formed of quartz doped with fluorine, $BF_3$ or the like at 20 mol % or less to obtain a low refractive index and a low fusion point, and the glass tube 120 formed of pure quartz. In this case, in the optical fiber 111, a refractive index of the core 111a is 1.45-1.46, a refractive index of the clad 111b is 1.44-1.47 and a fusing point of the clad 111b is 900° C. or more. In the glass tube 120, a fusing point of the glass tube 120 is 1400° C. or more.

In forming the optical fiber/glass tube fusion spliced structure 100, in part of the optical fiber/glass tube fusion spliced structure 100 including light passing through portions in an outer circumference portion of one end of the optical fiber 111 and in an inner circumference portion of the glass tube 120, by applying heat from the outside using laser ($CO_2$ laser or the like), a gas torch, discharge, electrothermo heater, or the like, the optical fiber 111 and the glass tube 120 are fusion spliced to form the fusion spliced portion 150. At this time, a heating temperature is set to be a temperature equal to or higher than a fusion point of the clad 111b of the optical fiber 111 and lower than a fusion point of the glass tube 120. Thus, only the clad 111b of the optical fiber 111 is fusion spliced with the glass tube 120 which has not been fusion spliced. Therefore, a major structural change due to fusion of both of the optical fiber 111 and the glass tube 120 can be avoided and light output characteristics of laser beam are not influenced by such a structural change.

Other than that, the structure, operation, formation method and effects of the optical fiber/glass tube fusion spliced structure 100 of Embodiment 7 are the same as those of Embodiment 5.

Embodiment 8

An optical fiber/glass tube fusion spliced structure 100 according to Embodiment 8 has the same outer appearance as that in Embodiment 7 and therefore will be described with reference to FIG. 13 and FIG. 14.

In this optical fiber/glass tube fusion spliced structure 100, an optical fiber 111 includes a core 111a formed of a material having a higher refractive index than a refractive index of a clad 111b. A glass tube 120 is formed so as to have a single-layer structure and is formed of a material having a lower laser beam absorption performance than a lower laser beam absorption performance of the clad 111b of the optical fiber 111. As such a structure, for example, the optical fiber 111 includes a core 111a formed of pure quartz and the clad 111b formed of lead glass or quartz having an OH value of 700 ppm or more and a high laser beam absorption performance, and the glass tube 120 is formed of pure quartz. In this case, the clad 111b of the optical fiber 111 has a high light absorption performance for laser beam having a wavelength of 9.2-10.8 μm and, on the other hand, the glass tube 120 has a very low light absorption performance for laser beam having a wavelength of 9.2-10.8 μm.

In forming the optical fiber/glass tube fusion spliced structure 100, in part of the optical fiber/glass tube fusion spliced structure 100 including light passing through portions in an outer circumference portion of one end of the optical fiber 111 and in an inner circumference portion of the glass tube 120, by irradiating laser beam having a predetermined wavelength to the part from the outside, the optical fiber 111 and the glass tube 120 are fusion spliced to form a fusion spliced portion 150. At this time, a wavelength of laser beam is set so that the clad 111b of the optical fiber 111 exhibits a high light absorption performance for the laser beam and the glass tube 120 exhibits a very low light absorption performance for the laser beam. Thus, only the clad 111b of the optical fiber 111, which is formed of a material having a high laser beam absorption performance, is fusion spliced with the glass tube 120 which has not been fused. Therefore, a major structural change due to fusion of both of the optical fiber 111 and the glass tube 120 can be avoided and light output characteristics of laser beam are not influenced by such a structural change.

Other than that, the structure, operation, formation method and effects of the optical fiber/glass tube fusion spliced structure 100 of Embodiment 8 are the same as those of Embodiment 7.

Other Embodiments

In each of Embodiments 1 through 8, the inner layer 121 of the glass tube 120 or the entire part of the clad 111b of the optical fiber 111 has a low fusion point or a high laser beam absorption performance. However, the optical fiber/glass tube fusion spliced structure of each of the above-described embodiments is not limited to the above-described structure but may be a structure in which at least a fusion spliced portion is formed of the above-described materials may be provided.

In each of Embodiments 1 through 8, the glass tube 120 having a cylindrical shape is fusion spliced with the optical fiber 111 and then the other end of the glass tube 120 is sealed. However, the glass tube 120 is not particularly limited to the structure but may be formed such that the glass tube 120 of which the other end is sealed beforehand so as to have a cap shape and then the glass tube 120 is fusion spliced with the optical fiber 111.

Figure 15:
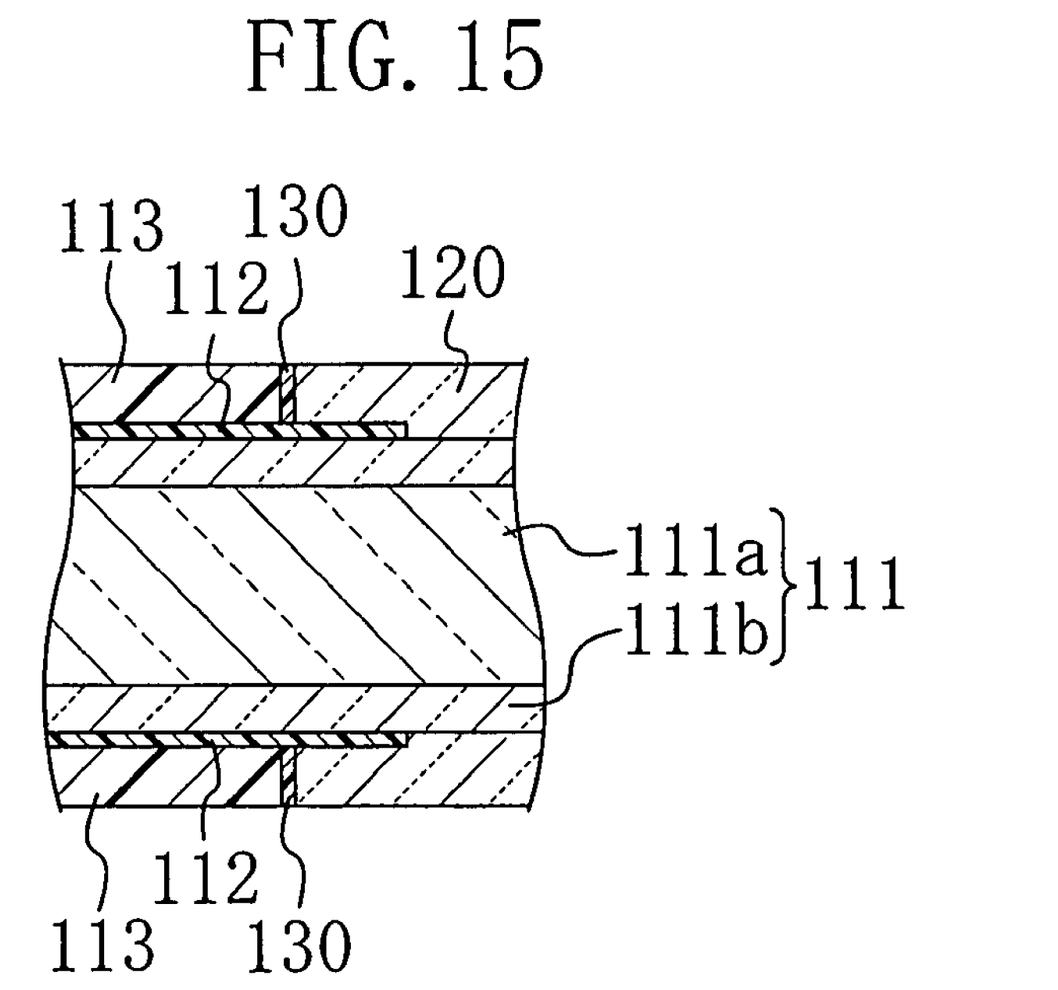
FIG. 15 is a view illustrating part of an optical fiber/glass tube fusion spliced structure according to another embodiment.

In each of Embodiments 1 through 8, parts of the glass tube 120 and the cover layer 113 having the same length are scaled. However, these parts are not limited to the above-described structures but, as shown in FIG. 15, a buffer layer 112 and a cover layer 113 may be formed so that the buffer layer 112 slightly protrudes from an end face of the cover layer 113 and a protruding part of the buffer layer 112 is inserted into the glass tube 120.

Figure 16A:
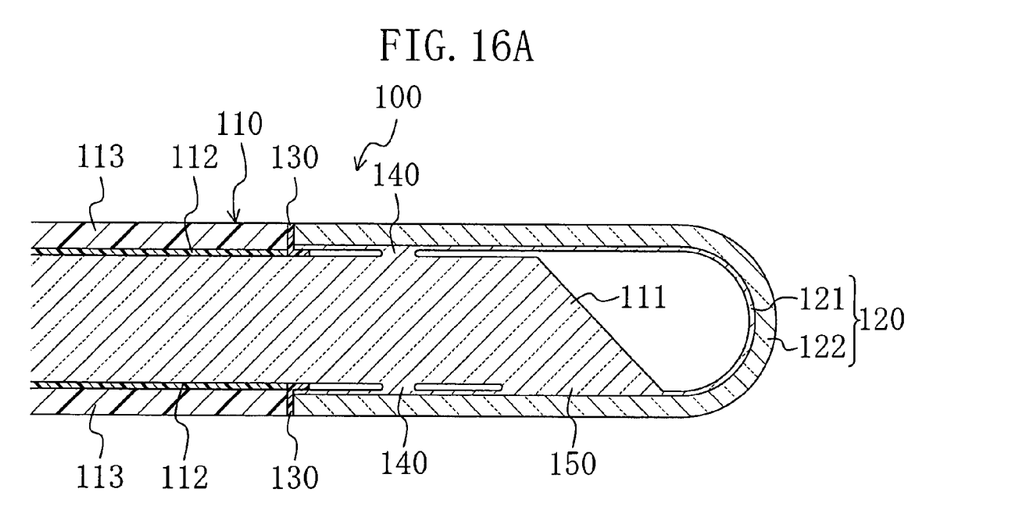
FIGS. 16A and 16B are longitudinal-sectional views of an optical fiber/glass tube fusion spliced structure according to another embodiment.
Figure 16B:
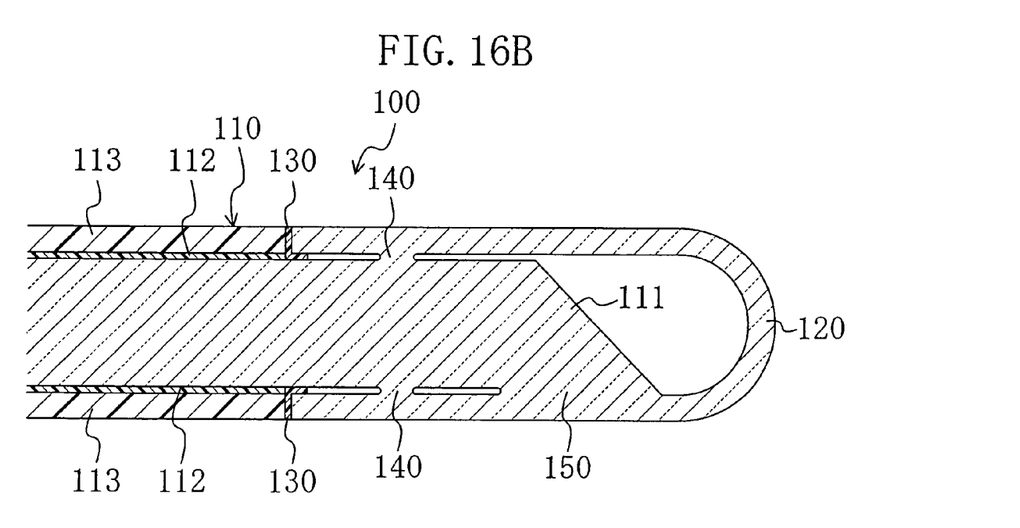

In each of Embodiments 1 through 4, part of the optical fiber/glass tube fusion spliced structure 100 extending along an entire circumference thereof is fusion spliced. In each of Embodiments 5 through 8, only part of the optical fiber/glass tube fusion spliced structure 100 including light passing through portions is fusion spliced. However, the optical fiber/glass tube fusion spliced structure of each of the above-described embodiments is not limited to the above-described structures. As shown in FIG. 16A, a structure formed of a combination of Embodiment 1 and Embodiment 5 or a structure formed of a combination of Embodiment 3 and Embodiment 7 may be provided. As shown in FIG. 16B, a structure formed of a combination of Embodiment 2 and Embodiment 6 or a structure formed of a combination of Embodiment 4 and Embodiment 8 may be provided.

On the present invention, many embodiments have been described above and modified examples of the embodiments have been discussed. However, the embodiments and modified examples have been described merely for the purpose of exemplifying the present invention. Further modified examples can be made by those persons skilled in the art within all aspects and the scope of the present invention defined only by the scope of claims appended to this specification.

What is claimed is:

1. An optical fiber/glass tube fusion spliced structure comprising:
    an optical fiber made of glass; and
    a glass tube through which the optical fiber is inserted,
    wherein at least in part of the optical fiber/glass tube fusion spliced structure, an outer circumference portion of the optical fiber and an inner circumference portion of the glass tube are fusion spliced, and wherein part of the fusion spliced portion of the glass tube is formed of a material having a lower fusion point than a fusion point of the fusion spliced portion of the optical fiber.

2. The optical fiber/glass tube fusion spliced structure of claim 1, wherein the optical fiber has an end portion inserted from one end of the glass tube through the glass tube and is adhered to the glass tube with an adhesive, and in part of the optical fiber/glass tube fusion spliced structure located closer to an end of the structure than the adhered portion of the optical fiber and the glass tube, the optical fiber and the glass tube are fusion spliced along an entire circumference.

3. The optical fiber/glass tube fusion spliced structure of claim 1, wherein the optical fiber has an end portion inserted from an end of the glass tube through the glass tube and is end-face-processed so that light is output from a side surface of the glass tube, and the optical fiber and the glass tube are fusion spliced so that the fusion spliced portion includes a light passing through portion in an outer circumference portion of the optical fiber and a light passing through portion in an inner circumference portion of the glass tube.

4. An optical fiber/glass tube fusion spliced structure comprising:

an optical fiber made of glass, and a glass tube through which the optical fiber is inserted, wherein at least in part of the optical fiber/glass tube fusion spliced structure, an outer circumference portion of the optical fiber and an inner circumference portion of the glass tube are fusion spliced, part of the fusion spliced portion located in one of the optical fiber and the glass tube is formed of a material having a lower fusion point than a fusion point of part of the fusion spliced portion located in the other, and wherein the optical fiber includes a core, a clad for covering the core and a supporting layer for covering the clad.

5. The optical fiber/glass tube fusion spliced structure of any one of claims 1, 2, 3 and 4, wherein the other end of the glass tube is sealed.

6. An optical fiber assembly comprising:

an optical fiber made of glass; and a glass tube through which an end portion of the optical fiber is inserted from one end of the glass tube and of which the other end is sealed, wherein the optical fiber is adhered to the glass tube with an adhesive, parts of the optical fiber and the glass tube located closer to respective ends thereof than the adhered portion of the optical fiber and the glass tube are fusion spliced along an entire circumference, and wherein part of the fusion spliced portion of the glass tube is formed of a material having a lower fusion point than a fusion point of the fusion spliced portion of the optical fiber.

7. An optical fiber assembly comprising:

an optical fiber made of glass; and a glass tube through which an end portion of the optical fiber is inserted from one end of the glass tube and of which the other end is sealed, wherein the optical fiber is end-face-processed so that light is output from a side surface of the glass tube, the optical fiber and the glass tube are fusion spliced so that the fusion spliced portion includes a light passing through portion in an outer circumference portion of the optical fiber and a light passing through portion in an inner circumference, and wherein part of the fusion spliced portion of the glass tube is formed of a material having a lower fusion point than a fusion point of the fusion spliced portion of the optical fiber.

8. An optical fiber/glass tube fusion spliced structure comprising:

an optical fiber made of glass; and a glass tube through which the optical fiber is inserted, and wherein at least in part of the optical fiber/glass tube fusion spliced structure, an outer circumference portion of the optical fiber and an inner circumference portion of the glass tube are fusion spliced, and the glass tube has a two-layer structure including an inner layer formed of a material having a higher light absorption performance for a laser beam having a predetermined wavelength than a light absorption performance of the fusion spliced portion of the optical fiber, and an outer layer formed of a material having a lower light absorption performance for the laser beam having the predetermined wavelength than the light absorption performance of the inner layer at an outer side of the inner layer.

9. The optical fiber/glass tube fusion spliced structure of claim 8, wherein the inner layer of the glass tube is formed of lead glass or quartz having an OH value of 700 ppm or more.

10. The optical fiber/glass tube fusion spliced structure of claim 8, wherein the optical fiber has an end portion inserted from one end of the glass tube through the glass tube and is adhered to the glass tube with an adhesive, and in part of the optical fiber/glass tube fusion spliced structure located closer to an end of the structure than the adhered portion of the optical fiber and the glass tube, the optical fiber and the glass tube are fusion spliced along an entire circumference.

11. The optical fiber/glass tube fusion spliced structure of claim 8, wherein the optical fiber has an end portion inserted from an end of the glass tube through the glass tube and is end-face-processed so that light is output from a side surface of the glass tube, and the optical fiber and the glass tube are fusion spliced so that the fusion spliced portion includes a light passing through portion in an outer circumference portion of the optical fiber and a light passing through portion in an inner circumference portion of the glass tube.

12. The optical fiber/glass tube fusion spliced structure of claim 8, wherein the optical fiber made of glass includes a core, a clad for covering the core and a supporting layer for covering the clad.

13. The optical fiber/glass tube fusion spliced structure of any one of claims 10 through 12, wherein the other end of the glass tube is sealed.

14. An optical fiber assembly comprising:

an optical fiber made of glass; and a glass tube through which an end portion of the optical fiber is inserted from one end of the glass tube and of which the other end is sealed, wherein the optical fiber is adhered to the glass tube with an adhesive, and parts of the optical fiber and the glass tube located closer to respective ends thereof than the adhered portion of the optical fiber and the glass tube are fusion spliced along an entire circumference, and the glass tube has a two-layer structure including an inner layer formed of a material having a higher light absorption performance for a laser beam having a predetermined wavelength than a light absorption performance of the fusion spliced portion of the optical fiber, and an outer layer formed of a material having a lower light absorption performance for the laser beam having the predetermined wavelength than the light absorption performance of the inner layer at an outer side of the inner layer.

15. An optical fiber assembly comprising:

an optical fiber made of glass; and a glass tube through which an end portion of the optical fiber is inserted from one end of the glass tube and of which the other end is sealed, wherein the optical fiber is end-face-processed so that light is output from a side surface of the glass tube, and the optical fiber and the glass tube are fusion spliced so that the fusion spliced portion includes a light passing through portion in an outer circumference portion of the optical fiber and a light passing through portion in an inner circumference portion of the glass tube, and the glass tube has a two-layer structure including an inner layer formed of a material having a higher light absorption performance for a laser beam having a predetermined wavelength than a light absorption performance of the fusion spliced portion of the optical fiber, and an outer layer formed of a material having a lower light absorption performance for the laser beam having the predetermined wavelength than the light absorption performance of the inner layer at an outer side of the inner layer.

16. An optical fiber/glass tube fusion spliced structure comprising:

an optical fiber made of glass; and a glass tube through which the optical fiber is inserted, wherein at least in part of the optical fiber/glass tube fusion spliced structure, an outer circumference portion of the optical fiber and an inner circumference portion of the glass tube are fusion spliced, and the glass tube have a two-layer structure including an inner layer formed of a material having a lower fusion point than a fusion point of a fusion spliced portion of the optical fiber and an outer layer formed of a material having a higher fusion point than the fusion point of the inner layer at an outer side of the inner layer.

17. An optical fiber/glass tube fusion spliced structure comprising:

an optical fiber made of glass, an end face of an end portion of which is formed to be a flat surface tilted from a fiber axis; and a glass tube through which the end portion of the optical fiber is inserted and which is adhered to the glass tube with an adhesive, wherein part of an outer circumference portion of the optical fiber not including a core and an inner circumference portion of the glass tube closer to respective ends of the optical fiber and the glass tube than the adhered portion of the optical fiber and the glass tube are fusion spliced along an entire circumference, and part of the fusion spliced portion located in one of the optical fiber and the glass tube is formed of a material having a lower fusion point than a fusion point of part of the fusion spliced portion located in the other.

18. An optical fiber/glass tube fusion spliced structure comprising:

an optical fiber made of glass; and a glass tube through which an end portion of the optical fiber is inserted and which is adhered to the glass tube with an adhesive, wherein part of an outer circumference portion of the optical fiber not including a core and an inner circumference portion of the glass tube located at the center portion between the end of the optical fiber and the adhered portion of the optical fiber and the glass tube are fusion spliced along an entire circumference, and part of the fusion spliced portion located in one of the optical fiber and the glass tube is formed of a material having a lower fusion point than a fusion point of part of the fusion spliced portion located in the other.

* * * * *